United States Patent [19]

Cohen

[11] 4,009,716

[45] Mar. 1, 1977

[54] NEEDLE-HUB ASSEMBLY FOR SYRINGES

[76] Inventor: Milton J. Cohen, 9201 Persimmon Tree Road, Potomac, Md. 20854

[22] Filed: Feb. 17, 1976

[21] Appl. No.: 658,613

[52] U.S. Cl. .......................... 128/218 NV; 128/221; 128/218 DA

[51] Int. Cl.² ......................................... A61M 5/32

[58] Field of Search ... 128/218 NV, 218 N, 218 DA, 128/218 F, 218 R, 218 M, 220, 221, 215, 216

[56] References Cited

UNITED STATES PATENTS

| 3,682,174 | 8/1972 | Cohen | 128/220 |
|---|---|---|---|
| 3,825,003 | 7/1974 | Kruck | 128/218 NV |
| 3,946,732 | 3/1976 | Hurscham | 128/218 DA X |

*Primary Examiner*—John D. Yasko
*Attorney, Agent, or Firm*—McDougall, Hersh & Scott

[57] ABSTRACT

A needle-hub assembly on a hypodermic syringe sealed at its open end by a sealing disc, the improvement wherein the needle and hub are displaced from a normally relaxed position to a tensioned position in response to movement to remove a needle cover from the assembly and wherein the needle and hub are thrust in the direction toward the sealing disc to pierce the sealing disc upon continued movement for removal of the cover.

9 Claims, 6 Drawing Figures

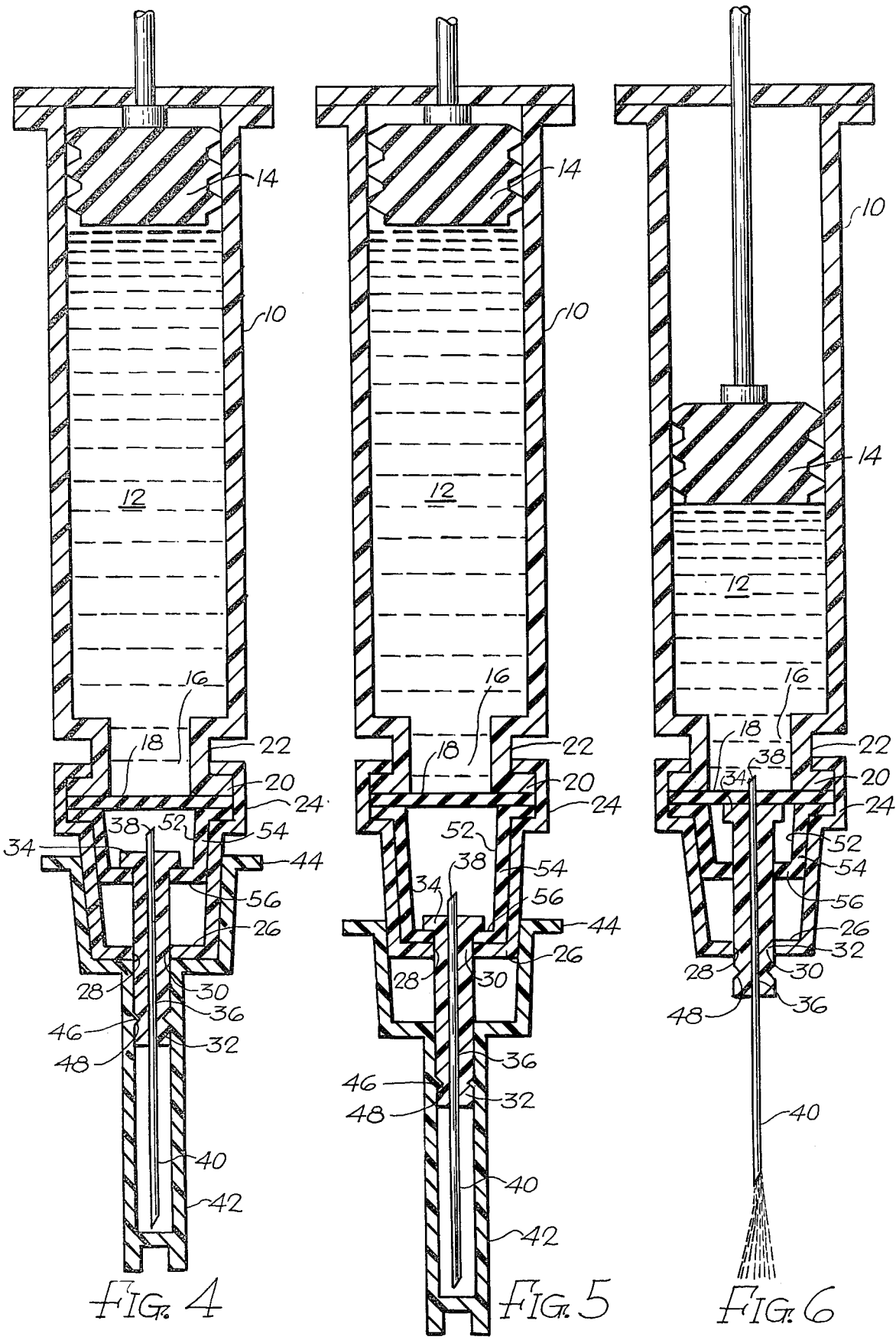

NEEDLE-HUB ASSEMBLY FOR SYRINGES

This invention relates to disposable hypodermic syringes, and more particularly to a hub assembly which mounts a hypodermic needle aseptically within and enclosure, and means for projecting the needle to pierce a sealing member for access to the interior of the syringe in response to removal of the enclosure.

In my U.S. Pat. Nos. 3,401,693, 3,682,174, and 3,757,779, description is made of disposable hypodermic syringes having a barrel, the open end of which is sealed by a sealing disc member. The hollow needle is mounted within a removable cover for aseptically housing the needle while protecting the needle against damage during periods of non-use. Means are provided for mounting the needle within the cover for piercing the sealing disc in order to gain access to the interior of the barrel, in response to removal of the cover.

Briefly described, use is made of a ferrule and a needle hub assembly, having a threaded portion at one end which threadably engages an internally threaded portion in the cover. The arrangement is such that, during assembly, the needle is urged to an advanced position against the action of a spring carried in the ferrule, thereby to enable the threaded portion of the hub to be engaged by the internally threaded portion of the cover, as the latter is secured into place. The cover thus engages the ferrule to maintain the ferrule in its advanced position until the cover is unscrewed, thus freeing the ferrule to enable the spring to snap to its relaxed position wherein the needle is projected to pierce the sealing member and project into the barrel for communication with the interior thereof.

One of the drawbacks to the described assembly arises from the needle to pre-tension the needle in the assembled hypodermic syringe. This leads to problems of assembly wherein inadvertent release of the needle during assembly, while in the tensioned relation, operates to project the needle as a missile not only to endanger the personnel, but also to result in loss of material and the inability to make use of automatic assembly procedures. The elements of the assembly are actually so small that proper retention, in assembly, becomes difficult, thereby to require complicated equipment and highly skilled labor for assembly.

U.S. Pat. No. 3,825,003 seeks to present a solution to this problem by specific design of the needle and hub assembly, but pre-tensioning of the needle is still required with all of its difficulties of assembly and continuing threat as a weapon, as aforesaid.

It is an object of this invention to provide a hub assembly of the type described in which the hypodermic needle is assembled in a relaxed state thereby to ease and simplify the assembly of the hub and thereby to eliminate the danger of providing a potential missile during the assembly of the hypodermic needle.

It is a related object to provide a hypodermic syringe of the type described in which the hypodermic needle is adapted to pierce the sealing disc mounted on the mouth of the barrel in response to removal of the needle cover, but in which the needle is placed under tension and released to pierce the sealing device only immediately prior to use and while the needle is safely confined within the cover; in which the needle is assembled and maintained in position of use in a non-tensioned relation, thereby to ease the assembly and eliminate the danger of flying off as a projectile; and in which a more effective force is generated immediately prior to use thereby to minimize misfire or ineffective firing of the needle through the sealing disc.

These and other objects and advantages of this invention will hereinafter appear and, for purposes of illustration, but not of limitation, embodiments of the invention are shown in the accompanying drawings in which:

FIG. 4 is a sectional view similar to that of FIG. 1 showing a modification in the needle-hub assembly;

FIg. 5 is a sectional view similar to that of FIG. 2 but with the needle-hub of FIG. 4; and FIG. 6 is a sectional view similar to that of FIG. 3 but with the modification of the needle-hub assembly of FIG. 4.

Figure 1:
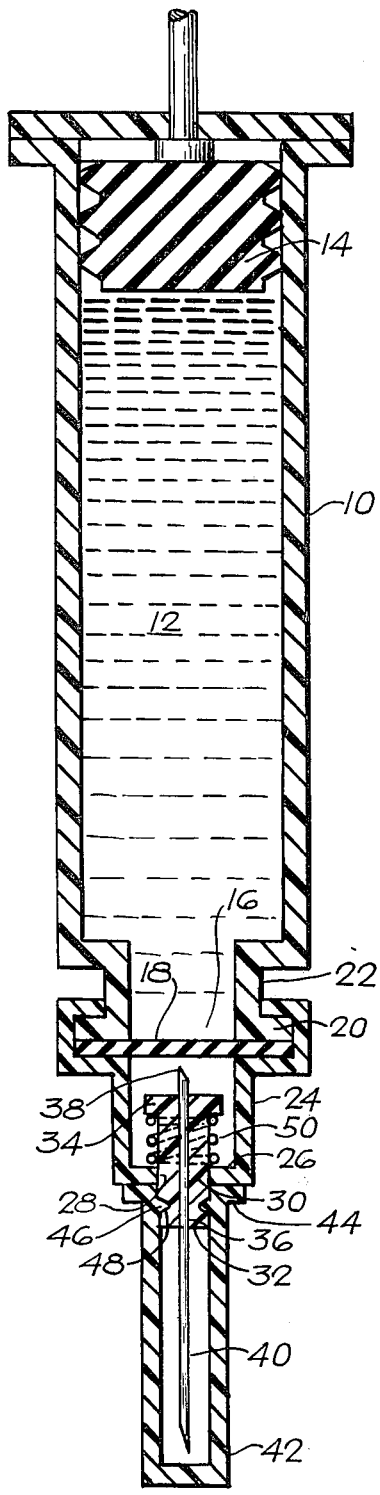
FIG. 1 is a schematic sectional elevational view through the axis of a hypodermic syringe having a hub assembly embodying the features of this invention, and in which elements are shown in their relative position prior to use.

The invention is illustrated by reference to a syringe comprising an elongate barrel 10 of glass or plastics, adapted to be filled with a liquid 12 to be dispensed from the barrel in response to displacement of a plunger 14 actually through the barrel. The barrel may be a single barrel for dispensing a liquid contained therein, as illustrated in U.S. Pat. No. 3,401,693, or it may be one of a series of telescoping barrels in which a liquid is displaced into the barrel for admixture with another liquid or soluble particulate material, as illustrated in the U.S. Pats. Nos. 3,682,194 and 3,757,779. Instead, the barrel 10 may be adapted to receive liquid drawn through the hypodermic needle in response to sub-atmospheric conditions generated within the barrel, as when the plunger is withdrawn actually through the barrel.

An open end 16 of the barrel 10 is sealed by a disc member 18 of resilient material which spans the open end of the barrel and is pressed into sealing engagement with the end face of the annular lip 20 which extends outwardly from the end of the neck portion 22 of the barrel 10. Sealing engagement is effected by means for securing a cup member 24 onto the end of the barrel, as by crimping the inner end portion of the cup member about the lip 20 with the sealing disc 18 in place.

The cup member 24 is in the form of a hollow cylindrical section which terminates in an end wall 26 having a central opening 28 of smaller dimension than the cylindrical section for the passage of a cylindrical portion 30 of a hub member 32 therethrough. The hub member has an inner end portion 34 of larger dimension than the opening 28 whereby outer displacement of the hub member is limited upon engagement of the end portion 34 with the end wall 26 of the cup member 24.

The hub is provided with an axially extending bore through which the hypodermic needle 36 extends with a small pointed end portion 38 of the needle projecting inwardly beyond the hub while the main portion 40 of the hollow hypodermic needle extends forward beyond the hub.

A needle cover 42 releasably engages the end portion of the hub extending forwardly beyond the opening of the cup member to encase the free end portion of the needle in normal position of non-use, to protect the needle, and to maintain antiseptic conditions. The needle cover is in the form of an elongate sleeve which is closed at the outer end and open at the inner end with the through extending end portion of the hub received in telescoping relation within the open end of the cover for sliding engagement therewith. An enlarged portion in the form of an annular flange 44 extends outwardly from the inner end of the cover to function as a stop against inward displacement of the hub member upon engagement of the end portion 44 with the base portion 26 of the cup member.

Means are provided releasably to latch the cover 42 onto the through extending portion of the hub 32 so that when force is applied to pull the cover off to expose the needle, the hub 32 will be displaced outwardly with the cover until resistance to movement exceeds the force latching the cover to the hub member. This will occur, for example, when the enlarged end portion 34 of the hub member comes into direct or indirect engagement with the base 26 of the cup member to prevent further outward displacement. In the illustrated modification, the latching means comprises a detente 46 which extends inwardly from an end portion of the sleeve releasably to be engaged in a recessed portion 48 in the telescoped end portion of the hub member.

Resilient means are provided to position the hub member within the cup with the enlarged inner end portion 34 intermediate the ends of the cup member with the pointed inner end 38 of the needle spaced a short distance outwardly of the sealing disc.

Figure 2:
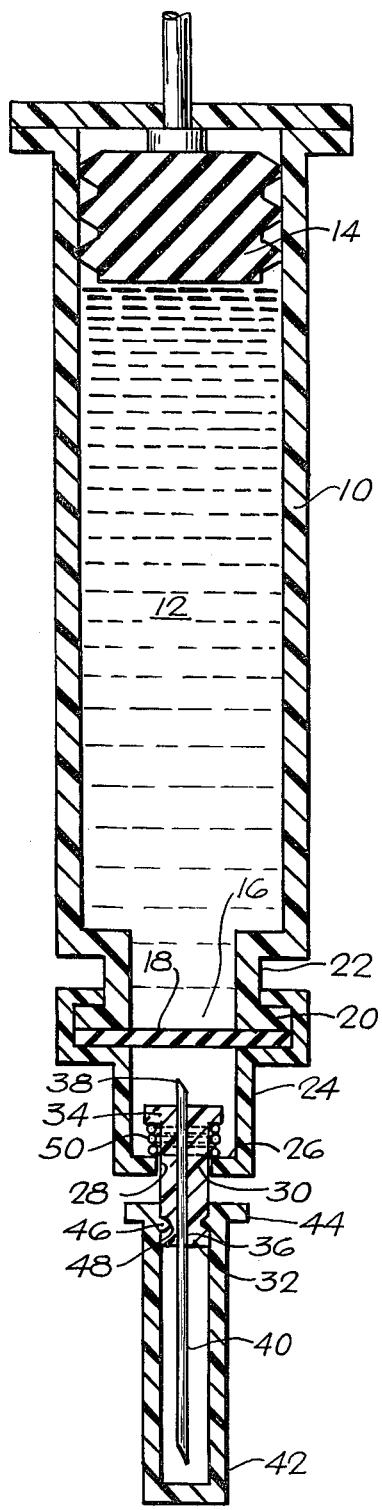
FIG. 2 is a sectional view of the syringe shown in FIG. 1 with the elements in their relative position during an intermediate stage of removal of the needle cover, prior to use.
Figure 3:
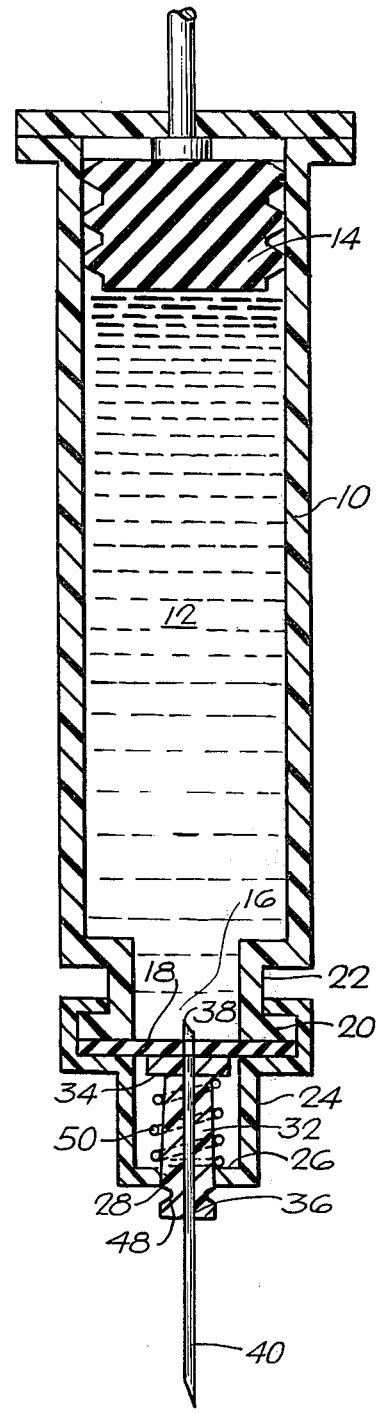
FIg. 3 is a sectional view of the syringe shown in FIG. 1 with the elements in their relative position after the needle cover has been removed.

In the modification shown in FIGS. 1–3, the resilient means comprises a coil spring 50 positioned about the hub member in the space between the enlarged flanged end portion 34 of the hub and the base 26 of the cup member. In the modification shown in FIGS. 4–6, the resilient means comprises a tubular member 52 of resilient material having a body portion 54 dimensioned to have a length less than the length of the cup member with a portion extending annularly outwardly from the inner end of the tubular member to enable the tubular member to be fixed onto the open end of the barrel when the sealing disc 18 is crimped by the cup onto the neck of the barrel. The outer end 56 of the tubular member is closed by an end wall having an opening through which the hub extends, with the inner end portion 34 of larger dimension within the tubular member.

Thus, when the elements are assembled, the elements are in a relaxed position shown in FIGS. 1 and 4 with the enlarged end portion of the hub spaced from the base 26 and with the end 38 of the needle spaced a short distance from the sealing disc 18.

When it is desired to take use of the syringe, the cover 42 is pulled forwardly to uncover the needle 36. The hub 26 moves forwardly with the cover 42, resulting in compression of the coil spring 50 in FIGS 1–3, or stretching of the tubular elastomeric member 52 in FIGS. 4–6. When further outward displacement of the hub is stopped by reason of the build-up of resilient force in the spring or elastic member, or certainly when the flange 34 comes into engagement with the base 26 of the cup, directly or indirectly through the resilient members, continued application of force to effect removal of the cover results in unlatching of the cover from the hub member whereby the spring in FIGS. 1–3, or the resilient tubular member in FIGS. 4–6, become effective, in the manner of a sling shot, to project the hub inwardly and thrust the needle point 38 through the sealing disc 18 for penetration into the interior of the barrel 10. The extent of inward displacement is defined by engagement of the end portion 34 with the outer face of the sealing disc 18. The penetrating portion of the needle is not disturbed since both the coil spring, in the modification shown in FIGS. 1–3, or the resilient member in the modification shown in FIGS. 4–6, automatically return to their relaxed position.

It will be apparent from the foregoing that the dimensioned force factors present in prior assemblies are completely eliminated in the assembly of the syringe embodying the features of this invention, and that the build-up of force sufficient to thrust the needle through the sealing disc is effected immediately prior to use in response to removal of the needle cover, and while the elements are confined thereby to eliminate the dangers characteristic of prior assemblies. The hypodermic syringe of this invention embodies safety factors which enhance their utility and enables simplification which enhances the use of mass-production techniques for assembly.

It will be understood that changes may be made in the details of construction, arrangement, and operation without departing from the spirit of the invention, especially as defined in the following claims.

I claim:

1. In a disposable hypodermic syringe having a barrel open at the forward end, a sealing disc fixed in sealing relation over the open end of the barrel, a cup member fixed onto the open end of the barrel, a hub member confined within the cup for movement in the direction toward and away from the open end of the barrel between extended and retracted positions, a hollow needle extending through the hub with an inner end portion extending inwardly beyond the hub and an outer portion extending forwardly beyond the hub, and a cover for enclosure of the needle portion extending forwardly of the hub, the improvement comprising means wherein the hub is located within the cup member normally intermediate between extended and retracted positions with the inner end of the needle spaced a short distance forwardly of the sealing disc and through the sealing disc when in retracted position, resilient means in position to be tensioned in response to movement of the hub from normal to extended position, and means releasably latching the cover with the hub for displacement of the hub from normal toward extended position responsive to displacement of the cover to expose the needle whereby, when the cover becomes disengaged from the hub, the tensioned resilient means becomes effective to thrust the needle and hub toward retracted position to pierce the sealing disc.

2. A syringe as claimed in claim 1 in which the resilient means is positioned in the path of the hub during movement of the hub from normal to extended position to effect tensioning of the resilient means responsive to movement of the hub from normal to extended position.

3. A syringe as claimed in claim 1 in which the resilient means comprises a coil spring positioned between a portion of the hub and a forward end portion of the cup for compression of the spring in response to movement of the hub toward extended position within the cup.

4. A syringe as claimed in claim 1 in which the resilient means comprises an elastic member secured to a rearward end portion of the cup and having an intermediate portion in position to be engaged by the hub during movement from normal to extended position.

5. A syringe as claimed in claim 4 in which the resilient means comprises a sleeve having a rearward end portion fixed to the rearward end of the cup and a forward end portion which is in position operatively to be engaged by the hub for movement therewith.

6. A syringe as claimed in claim 1 in which the resilient means is in a non-tensioned relation when the hub is in normal position and in which the resilient means releases the hub as a sling shot for movement toward retracted position in response to unlatching of the hub from the cover, when in an extended position.

7. A syringe as claimed in claim 1 which includes an enlarged portion on the inner end of the hub for engagement with the sealing disc as a stop when the hub is in retracted position and for direct or indirect engagement with the forward end portion of the cup when in extended position.

8. A syringe as claimed in claim 1 in which the means releasably latching the cover with the hub comprises a portion extending forwardly from the hub in telescoping relation with a rearward end portion of the cover, and interfitting grooves and detents in the telescoped portions releasably to interconnect the hub and cover.

9. A syringe as claimed in claim 8 in which the detent extends radially from the inner surface of the cover and a recessed portion in the telescoped portion of the hub for receiving the cover detent.

* * * * *